(12) United States Patent
Agrawal et al.

(10) Patent No.: US 9,688,993 B2
(45) Date of Patent: Jun. 27, 2017

(54) TOLL-LIKE RECEPTOR 9 ANTAGONIST AND METHODS OF USE THEREOF

(71) Applicant: Idera Pharmaceuticals, Inc., Cambridge, MA (US)

(72) Inventors: Sudhir Agrawal, Shrewsbury, MA (US); Daqing Wang, Bedford, MA (US); Fu-Gang Zhu, Bedford, MA (US)

(73) Assignee: IDERA PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/041,410

(22) Filed: Feb. 11, 2016

(65) Prior Publication Data

US 2016/0237437 A1   Aug. 18, 2016

Related U.S. Application Data

(60) Provisional application No. 62/115,753, filed on Feb. 13, 2015.

(51) Int. Cl.
   *C07H 21/04*  (2006.01)
   *C12N 15/117* (2010.01)
   *A61K 45/06*  (2006.01)

(52) U.S. Cl.
   CPC ............ *C12N 15/117* (2013.01); *A61K 45/06* (2013.01); *C12N 2310/17* (2013.01); *C12N 2310/3125* (2013.01); *C12N 2310/321* (2013.01); *C12N 2310/3341* (2013.01); *C12N 2310/3521* (2013.01); *C12N 2320/31* (2013.01)

(58) Field of Classification Search
   CPC ................................................... A61K 48/00
   See application file for complete search history.

(56) References Cited

U.S. PATENT DOCUMENTS

| | | | |
|---|---|---|---|
| 7,700,757 B2 | 4/2010 | Monteleone |
| 7,807,818 B2 | 10/2010 | Monteleone |
| 8,357,665 B2 | 1/2013 | Kandimalla et al. |
| 8,486,908 B2 | 7/2013 | Kandimalla et al. |
| 9,260,719 B2 | 2/2016 | Kandimalla et al. |
| 2009/0081198 A1 | 3/2009 | Kandimalla et al. |
| 2011/0009477 A1 | 1/2011 | Yu et al. |
| 2012/0015033 A1 | 1/2012 | Baroni et al. |

OTHER PUBLICATIONS

Krieg et al. (J. Clin. Inven. 117, 2007: 1184-1194).*
Lee, Y. S., et al., "Smad7 and Smad6 bind to discrete regions of Pellino-1 via their MH2 domains to mediate TGF-β1-induced negative regulation of IL-1 R/TLR signaling," Biochemical and Biophysical Research Communications, 393: 836-843 (2010).
Obermeier, F., et al., "CpG Motifs of Bacterial DNA Essentially Contribute to the Perpetuation of Chronic Intestinal Inflammation," Gastroenterology (2005), 129:913-927.
Bouladoux, N., et al., "Regulatory role of suppressive motifs from commensal DNA," Mucosal Immunol., (Nov. 2012) 5(6): 623-634.
Nagar, J., et al., "Therapeutic potential of chloroquine in a murine model of inflammatory bowel disease," International Immunopharmacology (2014), 21: 328-335.
Hiramatsu, Y., et al., "The anti-inflammatory effects of a high-frequency oligodeoxynucleotide from the genomic DNA of Lactobacillus casei," Int Immunopharmacol (2014), http://dx.doi.org/10.1016/j.intimp.2014.08.013.
Sun, S., et al., "TLR7/9 Antagonists as Therapeutics for Immune-Mediated Inflammatory Disorders," Inflammation & Allergy—Drug Targets (2007), 6: 223-235.

* cited by examiner

*Primary Examiner* — Kimberly Chong
(74) *Attorney, Agent, or Firm* — Morgan, Lewis & Bockius LLP

(57) ABSTRACT

The invention provides antagonist of TLR9 and methods of use thereof. These compounds inhibit or suppress TLR9-mediated signaling. The methods may have use in the prevention and treatment of diseases or disorders mediated by TLR9.

23 Claims, 7 Drawing Sheets

|  | PBS | 2 | 5 | 8 |
|---|---|---|---|---|
| CCR1 | 2.6 | 1.1 | 0.8 | 0.4 |
| CASP1 | -1.0 | -0.4 | -0.3 | 0.7 |
| CHIL1 | 5.3 | 3.5 | 3.5 | 3.0 |
| CXCL2 | 10.0 | 6.4 | 3.8 | 3.2 |
| CXCL3 | 9.4 | 5.6 | 3.3 | 1.3 |
| FPR1 | 7.5 | 3.9 | 3.6 | 2.7 |
| IL1b | 7.0 | 4.4 | 2.4 | 1.9 |
| IL1RN | 1.3 | 0.8 | 0.5 | 0.8 |
| ITGB2 | 1.6 | 0.0 | 0.5 | 0.5 |
| MMP10 | 4.0 | 2.2 | 1.9 | 1.9 |
| MMP3 | 3.3 | 0.3 | 0.5 | 0.7 |
| NOS2 | 4.0 | 1.5 | 1.7 | 1.1 |
| S100A8 | 6.9 | 3.8 | 2.0 | 1.2 |
| SAA3 | 10.6 | 5.9 | 5.9 | 4.6 |
| SELL | 4.5 | 2.0 | 2.6 | 0.4 |

FIG. 7

TOLL-LIKE RECEPTOR 9 ANTAGONIST AND METHODS OF USE THEREOF

RELATED APPLICATIONS

This application claims the benefit of U.S. Provisional Application No. 62/115,753, filed on Feb. 13, 2015, the contents of which are incorporated by reference in its entirety.

FIELD OF THE INVENTION

The invention generally relates to the field of immunology and immunotherapy, and more specifically to the use of oligonucleotides for inhibition and/or suppression of Toll-like Receptor 9 (TLR9)-mediated immune responses.

SUMMARY OF THE RELATED ART

Toll-like receptors (TLRs) are present on many cells of the immune system and have been shown to be involved in the innate immune response (Hornung, V. et al., (2002) J. Immunol. 168:4531-4537). In vertebrates, or mammals, this family consists of ten proteins called TLR1 to TLR10, which are known to recognize pathogen associated molecular patterns from bacteria, fungi, parasites, and viruses (Poltorak, A. et al. (1998) Science 282:2085-2088; Underhill, D. M., et al. (1999) Nature 401:811-815; Hayashi, F. et al. (2001) Nature 410:1099-1103; Zhang, D. et al. (2004) Science 303:1522-1526; Meier, A. et al. (2003) Cell. Microbiol. 5:561-570; Campos, M. A. et al. (2001) J. Immunol. 167: 416-423; Hoebe, K. et al. (2003) Nature 424: 743-748; Lund, J. (2003) J. Exp. Med. 198:513-520; Heil, F. et al. (2004) Science 303:1526-1529; Diebold, S. S., et al. (2004) Science 303:1529-1531; Hornung, V. et al. (2004) J. Immunol. 173:5935-5943). TLRs are a key means by which mammals recognize and mount an immune response to foreign molecules and also provide a means by which the innate and adaptive immune responses are linked (Akira, S. et al. (2001) Nature Immunol. 2:675-680; Medzhitov, R. (2001) Nature Rev. Immunol. 1:135-145). TLRs have also been shown to play a role in the pathogenesis of many diseases, including autoimmunity, infectious disease, and inflammation (Cook, D. N. et al. (2004) Nature Immunol. 5:975-979) and the regulation of TLR-mediated activation using appropriate agents may provide a means for disease intervention.

Some TLRs are located on the cell surface to detect and initiate a response to extracellular pathogens and other TLRs are located inside the cell to detect and initiate a response to intracellular pathogens. Table 1 provides a representation of TLRs, their cellular location, and the known agonists therefore (Diebold, S. S. et al. (2004) Science 303:1529-1531; Liew, F. et al. (2005) Nature 5:446-458; Hemmi H. et al. (2002) Nat Immunol 3:196-200; Jurk M. et al., (2002) Nat Immunol 3:499; Lee J. et al. (2003) Proc. Natl. Acad. Sci. USA 100:6646-6651); (Alexopoulou, L. (2001) Nature 413: 732-738).

TABLE 1

| TLR Molecule | Agonist |
|---|---|
| Cell Surface TLRs: | |
| TLR2 | bacterial lipopeptides |
| TLR4 | gram negative bacteria |

TABLE 1-continued

| TLR Molecule | Agonist |
|---|---|
| TLR5 | motile bacteria |
| TLR6 | gram positive bacteria |
| Endosomal TLRs: | |
| TLR3 | double stranded RNA viruses |
| TLR7 | single stranded RNA viruses |
| TLR8 | single stranded RNA viruses |
| TLR9 | unmethylated DNA |

Certain unmethylated CpG motifs present in bacterial and synthetic DNA have been shown to activate the immune system and induce antitumor activity. (Tokunaga T. et al., J. Natl. Cancer Inst. (1984) 72:955-962; Shimada S., et al., Jpn. H Cancer Res, 1986, 77, 808-816; Yamamoto S., et al., Jpn. J. Cancer Res., 1986, 79, 866-73). Other studies using antisense oligonucleotides containing CpG dinucleotides have been shown to stimulate immune responses (Zhao Q., et al. (1996) Biochem. Pharmacol. 26:173-182). Subsequent studies demonstrated that TLR9 recognizes unmethylated CpG motifs present in bacterial and synthetic DNA (Hemmi, H. et al. (2000) Nature 408:740-745). Other modifications of CpG-containing phosphorothioate oligonucleotides can also affect their ability to act as modulators of immune response through TLR9 (see, e.g., Zhao et al., Biochem. Pharmacol. (1996) 51:173-182; Zhao et al. (1996) Biochem Pharmacol. 52:1537-1544; Zhao et al. (1997) Antisense Nucleic Acid Drug Dev. 7:495-502; Zhao et al. (1999) Bioorg. Med. Chem. Lett. 9:3453-3458; Zhao et al. (2000) Bioorg. Med. Chem. Lett. 10:1051-1054; Yu, D. et al. (2000) Bioorg. Med. Chem. Lett. 10:2585-2588; Yu, D. et al. (2001) Bioorg. Med. Chem. Lett. 11:2263-2267; and Kandimalla, E. et al. (2001) Bioorg. Med. Chem. 9:807-813). In addition, structure activity relationship studies have allowed identification of synthetic motifs and novel DNA-based compounds that induce specific immune response profiles that are distinct from those resulting from unmethylated CpG dinucleotides. (Kandimalla, E. et al. (2005) Proc. Natl. Acad. Sci. USA 102:6925-6930. Kandimalla, E. et al. (2003) Proc. Nat. Acad. Sci. USA 100:14303-14308; Cong, Y. et al. (2003) Biochem Biophys Res. Commun.310:1133-1139; Kandimalla, E. et al. (2003) Biochem. Biophys. Res. Commun. 306:948-953; Kandimalla, E. et al. (2003) Nucleic Acids Res. 31:2393-2400; Yu, D. et al. (2003) Bioorg. Med. Chem.11:459-464; Bhagat, L. et al. (2003) Biochem. Biophys. Res. Commun.300:853-861; Yu, D. et al. (2002) Nucleic Acids Res. 30:4460-4469; Yu, D. et al. (2002) J. Med. Chem.45:4540-4548. Yu, D. et al. (2002) Biochem. Biophys. Res. Commun.297:83-90; Kandimalla. E. et al. (2002) Bioconjug. Chem.13:966-974; Yu, D. et al. (2002) Nucleic Acids Res. 30:1613-1619; Yu, D. et al. (2001) Bioorg. Med. Chem. 9:2803-2808; Yu, D. et al. (2001) Bioorg. Med. Chem. Lett. 11:2263-2267; Kandimalla, E. et al. (2001) Bioorg. Med. Chem. 9:807-813; Yu, D. et al. (2000) Bioorg. Med. Chem. Lett. 10:2585-2588; Putta, M. et al. (2006) Nucleic Acids Res. 34:3231-3238).

The selective localization of TLRs and the signaling generated therefrom, provides some insight into their role in the immune response. The immune response involves both an innate and an adaptive response based upon the subset of cells involved in the response. For example, the T helper (Th) cells involved in classical cell-mediated functions such as delayed-type hypersensitivity and activation of cytotoxic T lymphocytes (CTLs) are Th1 cells. This response is the body's innate response to antigen (e.g. viral infections, intracellular pathogens, and tumor cells), and results in a secretion of IFN-gamma and a concomitant activation of CTLs. Alternatively, the Th cells involved as helper cells for B-cell activation are Th2 cells. Th2 cells have been shown to be activated in response to bacteria and parasites and may mediate the body's adaptive immune response (e.g. IgE production and eosinophil activation) through the secretion of IL-4 and IL-5. The type of immune response is influenced by the cytokines produced in response to antigen exposure and the differences in the cytokines secreted by Th1 and Th2 cells may be the result of the different biological functions of these two sub sets.

While activation of TLRs is involved in mounting an immune response, an uncontrolled stimulation of the immune system through TLRs may exacerbate certain diseases. Recent studies have shown that toll-like receptor recognition of bacterial DNA from commensal flora resulted in activation of an innate immune response leading to the perpetuation of chronic inflammation in the gut (see e.g., Hiramatsu et al. (2014) International Immunopharmacology; Bouladoux et al. (2012) Mucosal Immunol. 5(6): 623-634; Nagar et al. (2014) International Immunopharmacology 21: 328-335; Sun et al., (2007) Inflammation & Allergy-Drug Targets, Vol. 6, No. 4; and Obermeier et al., (2005) GASTROENTEROLOGY,129:913-927). Current available therapies directed to treating this chronic inflammation are limited due to their serious adverse effects. Thus there is a need for compounds and compositions useful in many clinically relevant applications for treating and preventing diseases and disorders with an immune stimulatory component.

BRIEF SUMMARY OF THE INVENTION

The invention provides compounds that act as distinct antagonists of TLR9 and methods of using such compounds to antagonize, inhibit, suppress or prevent TLR9-mediated immune stimulation. The compounds and compositions that preferentially antagonize, inhibit, suppress or prevent the activity of TLR9 have the sequence (SEQ ID NO: 1): 5'-$(N_1)_mCG(N_2)_p$-3', wherein $N_1$ and $N_2$ are independently any nucleotide, m is number from 0 to about 5, p is a number from about 6 to about 35, C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; and provided that at each instance that $N_1$ and/or $N_2$ comprise a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto. In some embodiments, the compounds and compositions that preferentially antagonize, inhibit, suppress or prevent the activity of TLR9 have the following sequence (SEQ ID NO: 2): 5'-$(N_1)_nCGN_2)_rCG(N_3)_z$-3', wherein $N_1$, $N_2$, and $N_3$ are independently any nucleotide, n is 2, r is 11, z is 3, C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto, and provided that at each instance that $N_1$, $N_2$ and/or $N_3$ comprise a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto.

In some embodiments, the compounds and compositions that preferentially antagonize, inhibit, suppress or prevent the activity of TLR9 comprise the sequence 5'-$G_xTC^*G^*(N_1)_mCC^*G^*CAG_x(N_2)_p$-3' (SEQ ID NO: 3), wherein Gx is 2'-deoxyguanosine or 2'-deoxyguanosine methylphosphonate, $N_1$ is any nucleotide and $N_2$ is any nucleotide, wherein m is 10 and p is 0 or 1, and wherein C* is a nucleotide comprising a nitrogenous base selected from the group consisting of cytosine, 5-methyl-2'-deoxycytosine and 2'-O-methylcytosine and G* is a nucleotide comprising a nitrogenous base selected from the group consisting of guanine, 5-methyl-2'-deoxyguanosine and 2'-O-methylguanine, provided that at least one of the nucleotides C* or G* comprises a methylated nitrogenous base; and provided that at each instance that $N_1$ comprises a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto.

Thus, the invention provides a method for inhibiting a TLR9-mediated immune response in a vertebrate, or mammal, the method comprising administering to the mammal a compound, or a composition comprising the compound, according to the invention in a pharmaceutically effective amount.

In some embodiments, the compounds may comprise at least two oligonucleotides, wherein at least two oligonucleotides are covalently linked via a direct nucleotide to nucleotide linkage at their 3' ends through the 3' positions of the sugars or through a modified sugar or modified nucleobase or via a non-nucleotide linker at their 3' ends through the 3' positions of the sugars or through a modified sugar or modified nucleobase.

The invention further provides a method for suppressing or inhibiting the activity of a TLR9 agonist comprising administering a compound according to the invention, wherein the compound is administered at the same time, prior to or after the TLR9 agonist.

The invention further provides a method for therapeutically treating a vertebrate, or mammal, having a disease mediated by TLR9, such method comprising administering to the mammal a compound according to the invention in a pharmaceutically effective amount. In preferred embodiments, the disease is cancer, an autoimmune disease or disorder, airway inflammation, an inflammatory disease or disorder, infectious disease, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma or a disease caused by a pathogen. Preferred autoimmune diseases and disorders include without limitation lupus erythematosus, multiple sclerosis, type I diabetes mellitus, irritable bowel syndrome, Crohn's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis (also known as "giant cell arteritis"), vasculitis, vitiligo, vulvodynia, and Wegener's granulomatosis. Preferred inflammatory diseases and disorders include without limitation airway inflammation, asthma, autoimmune diseases, chronic inflammation, chronic prostatitis, glomerulonephritis, Behçet's disease, hypersensitivities, inflammatory bowel disease, reperfusion injury, rheumatoid arthritis, transplant rejection, ulcerative colitis, uveitis, conjunctivitis, and vasculitis.

The invention further provides a method for preventing a disease mediated by TLR9, such method comprising administering to the mammal a compound according to the invention in a pharmaceutically effective amount. In preferred embodiments, the disease is cancer, autoimmune diseases or disorders, airway inflammation, inflammatory diseases or disorders, infectious disease, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma or a disease caused by a pathogen in a vertebrate, or mammal, such method comprising administering to the mammal a compound according to the invention in a pharmaceutically effective amount. Preferred autoimmune diseases and disorders include without limitation lupus erythematosus, multiple sclerosis, type I diabetes mellitus, irritable bowel syndrome, Crohn's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis (also known as "giant cell arteritis"), vasculitis, vitiligo, vulvodynia, and Wegener's granulomatosis. Preferred inflammatory diseases and disorders include without limitation airway inflammation, asthma, autoimmune diseases, chronic inflammation, chronic prostatitis, glomerulonephritis, Behçet's disease,_hypersensitivities, inflammatory bowel disease, reperfusion injury, rheumatoid arthritis, transplant rejection, ulcerative colitis, uveitis, conjunctivitis, and vasculitis.

In some preferred embodiments, the compound according to the invention is administered in combination with one or more vaccines, antigens, antibodies, cytotoxic agents, allergens, antibiotics, antisense oligonucleotides, TLR agonists, TLR antagonists, peptides, proteins, gene therapy vectors, DNA vaccines, adjuvants, kinase inhibitors or co-stimulatory molecules or combinations thereof. In some preferred embodiments, the route of administration is parenteral, mucosal delivery, oral, sublingual, transdermal, topical, inhalation, intranasal, aerosol, intraocular, intratracheal, intrarectal, intragastric, vaginal, by gene gun, dermal patch or in eye drop or mouthwash form.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 7 depicts the colonic gene expression in a TNBS-induced colitis mouse model after administration of compounds according to the invention.

DETAILED DESCRIPTION OF THE PREFERRED EMBODIMENTS

Figure 1:
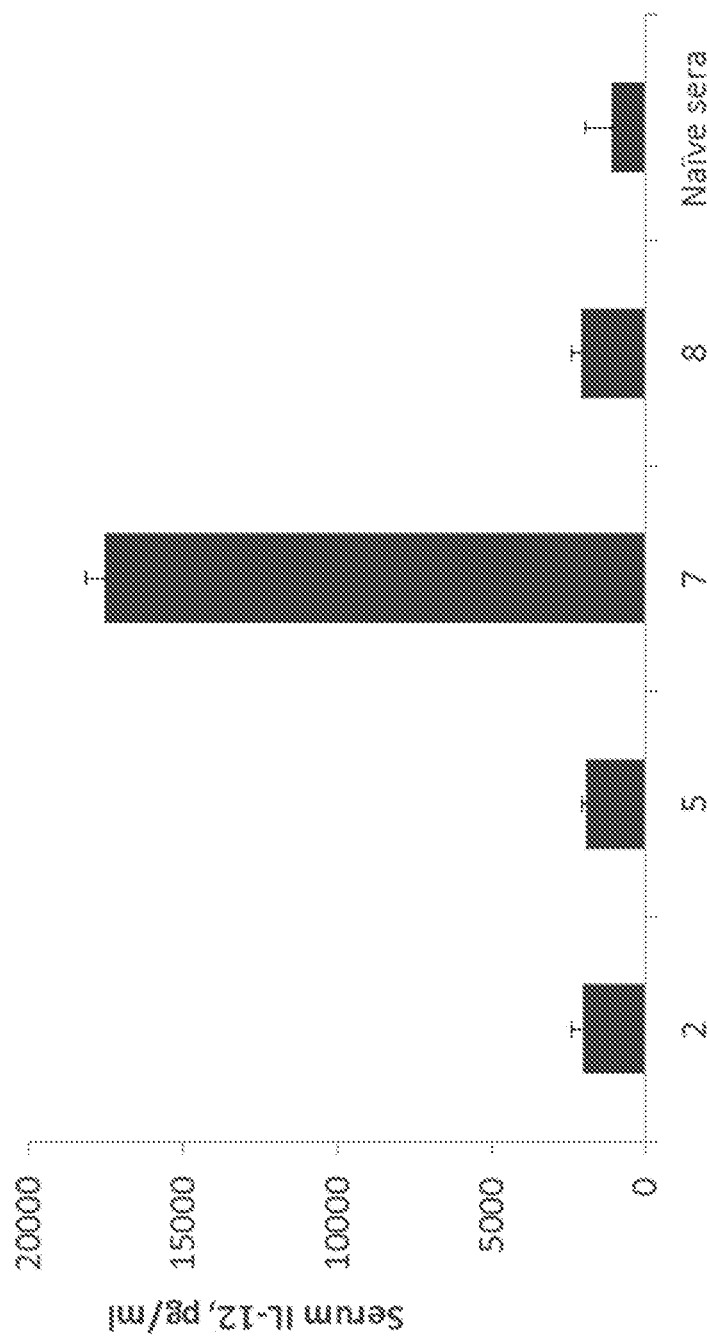
FIG. 1 shows that the compounds according to the invention do not induce a TLR9-mediated immune response.

The present invention relates to the therapeutic use of oligonucleotide compounds as immune modulatory agents for immunotherapy applications. The invention provides compounds that provide immune inhibition through their interaction with TLR9. Specifically, the invention provides compounds as antagonists of toll-like receptor 9 (TLR9) to inhibit and/or suppress a TLR9-mediated immune response. These compounds have chemical modifications, and/or internucleotide linkages, and/or linkers between oligonucleotides that provide their inhibition or suppression of TLR9-mediated signaling in response to endogenous and/or exogenous TLR9 ligands or agonists. The references cited herein reflect the level of knowledge in the field and are hereby incorporated by reference in their entirety. Any conflicts between the teachings of the cited references and this specification shall be resolved in favor of the latter.

The invention further provides methods for suppressing an immune response induced by TLR9 and can be used for immunotherapy applications such as, but not limited to, treatment of cancer, autoimmune disorders, asthma, respiratory allergies, food allergies, skin allergies, systemic lupus erythematosus (SLE), arthritis, pleurisy, chronic infections, inflammatory diseases, inflammatory bowel syndrome, sepsis, and bacteria, parasitic, and viral infections in adult and pediatric human and veterinary applications. Thus, the invention provides compounds having optimal levels of immune modulatory effect for immunotherapy and methods for making and using such compounds. In addition, compounds of the invention are useful in combination with, for example, vaccines, antigens, antibodies, allergens, chemotherapeutic agents (both chemotherapy and targeted therapies), and/or antisense oligonucleotides for prevention and treatment of diseases.

DEFINITIONS

The term "oligonucleotide" generally refers to a polynucleoside comprising a plurality of linked nucleoside units. Such oligonucleotides can be obtained from existing nucleic acid sources, including genomic or cDNA, but are preferably produced by synthetic methods. In preferred embodiments each nucleoside unit can encompass various chemical modifications and substitutions as compared to wild-type oligonucleotides, including but not limited to modified nucleoside base and/or modified sugar unit. Examples of chemical modifications are known to the person skilled in the art and are described, for example, in Uhlmann E. et al. (1990) Chem. Rev. 90:543; "Protocols for Oligonucleotides and Analogs" Synthesis and Properties & Synthesis and Analytical Techniques, S. Agrawal, Ed, Humana Press, Totowa, USA 1993; and Hunziker, J. et al. (1995) Mod. Syn. Methods 7:331-417; and Crooke, S. et al. (1996) Ann. Rev. Pharm. Tox. 36:107-129. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., ($R_P$)- or ($S_P$)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate or phosphorodithioate linkages or combinations thereof.

The term "2'-substituted ribonucleoside" or "2'-substituted arabinoside" generally includes ribonucleosides or arabinonucleosides in which the hydroxyl group at the 2' position of the pentose moiety is substituted to produce a 2'-substituted or 2'-O-substituted ribonucleoside. In certain embodiments, such substitution is with a lower hydrocarbyl group containing 1-6 saturated or unsaturated carbon atoms, with a halogen atom, or with an aryl group having 6-10 carbon atoms, wherein such hydrocarbyl, or aryl group may be unsubstituted or may be substituted, for example, with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-amino, 2'-fluoro, 2'-allyl, 2'-O-alkyl and 2'-propargyl ribonucleosides or arabinosides, 2'-O-methylribonucleosides or 2'-O-methylarabinosides and 2'-O-methoxyethoxyribonucleosides or 2'-O-methoxyethoxyarabinosides.

The term "3'", when used directionally, generally refers to a region or position in a polynucleotide or oligonucleotide 3' (downstream) from another region or position in the same polynucleotide or oligonucleotide.

The term "5'", when used directionally, generally refers to a region or position in a polynucleotide or oligonucleotide 5' (upstream) from another region or position in the same polynucleotide or oligonucleotide.

The term "about" generally means that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above.

The term "agonist" generally refers to a substance that binds to a receptor of a cell and induces a response. An agonist can be a naturally occurring substance such as bacterial DNA or a synthetic composition. A synthetic agonist often mimics the action of a naturally occurring substance such as a ligand.

The term "antagonist" generally refers to a substance that attenuates, inhibits or suppresses the effects of an agonist or ligand.

The term "adjuvant" generally refers to a substance which, when added to an immunogenic agent such as vaccine or antigen, enhances or potentiates an immune response to the agent in the recipient host upon exposure to the mixture.

The term "airway inflammation" generally includes, without limitation, asthma.

The term "allergen" generally refers to an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic immune response upon exposure to the molecule.

The term "allergy" generally refers to an inappropriate immune response characterized by inflammation and includes, without limitation, food allergies and respiratory allergies.

The term "antigen" generally refers to a substance that is recognized and selectively bound by an antibody or by a T cell antigen receptor, resulting in induction of an immune response. Antigens may include but are not limited to peptides, proteins, nucleosides, nucleotides, and combinations thereof. Antigens may be natural or synthetic and generally induce an immune response that is specific for that antigen.

The terms "autoimmune disease" and autoimmune disorder" generally refer to diseases or disorders in which "self" components undergo attack by the immune system.

The term "TLR9-mediated disease" or TLR9-mediated disorder" generally means any pathological condition for which activation of one or more TLR9 is a contributing factor. Such conditions include but are not limited, cancer, autoimmune diseases or disorders, airway inflammation, inflammatory diseases or disorders, infectious diseases, skin disorders, allergy, asthma or diseases caused by a pathogen.

The term "physiologically acceptable" generally refers to a material that does not interfere with the effectiveness of a compound or composition according to the invention and that is compatible with a biological system such as a cell, cell culture, tissue or organism. Preferably, the biological system is a living organism, such as a vertebrate, or mammal.

The term "carrier" generally encompasses any excipient, diluent, filler, salt, buffer, stabilizer, solubilizer, oil, lipid, lipid containing vesicle, microspheres, liposomal encapsulation or other material well known in the art for use in pharmaceutical formulations. It will be understood that the characteristics of the carrier, excipient or diluent will depend on the route of administration for a particular application. The preparation of pharmaceutically acceptable formulations containing these materials is described in, for example, *Remington's Pharmaceutical Sciences*, 18th Edition, ed. A. Gennaro, Mack Publishing Co., Easton, Pa., 1990.

The term "co-administration" generally refers to the administration of at least two different substances sufficiently close in time. Co-administration refers to simultaneous administration, as well as temporally spaced order of up to several days apart, of at least two different substances in any order, either in a single dose or separate doses.

The term "complementary" generally means having the ability to hybridize to a nucleic acid. Such hybridization is ordinarily the result of hydrogen bonding between complementary strands, preferably to form Watson-Crick or Hoogsteen base pairs, although other modes of hydrogen bonding, as well as base stacking can also lead to hybridization.

The term an "effective amount" or a "sufficient amount" generally refers to an amount sufficient to affect a desired biological effect, such as beneficial results. Thus, an "effective amount" or "sufficient amount" will depend upon the context in which it is being administered. In the context of administering a compound or composition that modulates an immune response to a co-administered antigen, an effective amount of a compound or composition according to the invention and antigen is an amount sufficient to achieve the desired modulation, inhibition or suppression as compared to the immune response obtained when the antigen is administered alone. An effective amount may be administered in one or more administrations.

The term "in combination with" generally means administering two or more agents (e.g., a TLR9 antagonist compound according to the invention and another agent) such that there is an overlap of an effect of each agent on the patient. Such administration may be done in any order, including simultaneous administration, as well as temporally spaced order from a few seconds up to several days apart. In some embodiments, the administration of the agents are spaced sufficiently close together such that a combinatorial effect is achieved. Such combination treatment may also include more than a single administration of the compound according to the invention and/or independently the other agent. The administration of the compound according to the invention and the other agent may be by the same or different routes. In some embodiments, administration of at least one agent is made while the other agent is still present at a therapeutic level in the subject.

The term "individual" or "patient" or "subject" or "vertebrate" generally refers to a mammal. Mammals generally include, but are not limited to, humans, non-human primates, rats, mice, cats, dogs, horses, cattle, cows, pigs, sheep, and rabbits.

The term "kinase inhibitor" generally refers to molecules that antagonize or inhibit phosphorylation-dependent cell signaling and/or growth pathways in a cell. Kinase inhibitors may be naturally occurring or synthetic and include small molecules that have the potential to be administered as oral therapeutics. Kinase inhibitors have the ability to rapidly and specifically inhibit the activation of the target kinase molecules. Protein kinases are attractive drug targets, in part because they regulate a wide variety of signaling and growth pathways and include many different proteins. As such, they have great potential in the treatment of diseases involving kinase signaling, including cancer, cardiovascular disease, inflammatory disorders, diabetes, macular degeneration and neurological disorders. Examples of kinase inhibitors include sorafenib (NEXAVAR®), SUTENT®, DASATINIB™, ZACTIMA™, TYKERB™ and STI571.

The term "nucleoside" generally refers to compounds consisting of a sugar, usually ribose or deoxyribose, and a purine or pyrimidine base.

The term "nucleotide" generally refers to a nucleoside comprising a phosphate group attached to the sugar.

As used herein, the term "pyrimidine nucleoside" refers to a nucleoside wherein the base component of the nucleoside is a pyrimidine base (e.g., cytosine (C) or thymine (T) or Uracil (U)). Similarly, the term "purine nucleoside" refers to a nucleoside wherein the base component of the nucleoside is a purine base (e.g., adenine (A) or guanine (G)).

The terms "analog" or "derivative" can be used interchangeable to generally refer to any purine and/or pyrimidine nucleotide or nucleoside that has a modified base and/or sugar. A modified base is a base that is not guanine, cytosine, adenine, thymine or uracil. A modified sugar is any sugar that is not ribose or 2'deoxyribose and can be used in the backbone for an oligonucleotide.

The term "inhibiting" or "suppressing" generally refers to a decrease in or a prevention of a response or qualitative difference in a response, which could otherwise arise from eliciting and/or stimulation of a response.

The term "non-nucleotide linker" generally refers to any linkage or moiety that can link or be linked to the oligonucleotides other than through a phosphorous-containing linkage. Preferably such linker is from about 2 angstroms to about 200 angstroms in length.

The term "nucleotide linkage" generally refers to a direct 3'-5' linkage that directly connects the 3' and 5' hydroxyl groups of two nucleosides through a phosphorous-containing linkage.

The term "treatment" generally refers to an approach intended to obtain a beneficial or desired results, which may include alleviation of symptoms and/or delaying and/or ameliorating the progression of a disease or disorder.

The invention provides methods for inhibiting or suppressing TLR9-mediated induction of an immune response in a mammal, such methods comprising administering to the mammal a compound according to the invention comprising the sequence (SEQ ID NO: 1): 5'-$(N_1)_m CG(N_2)_p$-3', wherein $N_1$ and $N_2$ are independently any nucleotide, m is number from 0 to about 5, p is a number from about 6 to about 35, C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; and provided that at each instance that $N_1$ and/or $N_2$ comprise a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto. In some embodiments, the compounds and compositions that preferentially antagonize, inhibit, suppress or prevent the activity of TLR9 have the following sequence (SEQ ID NO: 2): 5'-$(N_1)_n CG(N_2)_r CG(N_3)_z$-3', wherein $N_1$, $N_2$, and $N_3$ are independently any nucleotide, n is 2, r is 11, z is 3, C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto, and provided that at each instance that $N_1$, $N_2$ and/or $N_3$ comprise a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto. In some embodiments, the mammal is a human. In preferred embodiments, the compound is administered to a mammal in need of immune suppression. In preferred embodiments, the compound is selected from the group consisting of 5'-$GTC_1GCCCCTTCTCCCC_1GCAG$-3', 5'-$GTC_1GCCCCTTCTCCCC_1GCAGC$-3', 5'-$G_1TC_1GCCCCTTCTCCCC_1GCAG_1$-3', 5'-$GTC_1GTTTACCTCTTCC_1GCAGC$-3', and 5'-$G_1TC_1GCCCCTTCTCCCC_1GCAG_1C$-3', wherein $C_1$ is 5-methyl-dC and $G_1$ is 2'-deoxyguanosine methylphosphonate.

In some embodiments, the invention provides methods for inhibiting or suppressing TLR9-mediated induction of an immune response in a mammal, such methods comprising administering to the mammal a compound according to the invention comprising the sequence 5'-$G_xTC*G*(N_1)_mCC*G*CAG_x(N_2)_p$-3' (SEQ ID NO: 3), wherein Gx is 2'-deoxyguanosine or 2'-deoxyguanosine methylphosphonate, $N_1$ is any nucleotide and $N_2$ is any nucleotide, wherein m is 10 and p is 0 or 1, and wherein C* is a nucleotide comprising a nitrogenous base selected from the group consisting of cytosine, 5-methyl-2'-deoxycytosine and 2'-O-methylcytosine and G* is a nucleotide comprising a nitrogenous base selected from the group consisting of guanine, 5-methyl-2'-deoxyguanosine and 2'-O-methylguanine, provided that at least one of the nucleotides C* or G* comprises a methylated nitrogenous base; and provided that at each instance that $N_1$ comprises a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto. In some embodiments, the mammal is a human. In preferred embodiments, the compound is administered to a mammal in need of immune suppression. In preferred embodiments, the compound is selected from the group consisting of 5'-$GTC_1GCCCCTTCTCCCC_1GCAG$-3' (SEQ ID NO: 4), 5'-$GTC_1GCCCCTTCTCCCC_1GCAGC$-3' (SEQ ID NO: 5), 5'-$G_1TC_1GCCCCTTCTCCCC_1GCAG_1$-3' (SEQ ID NO: 6), 5'-$GTC_1GTTTACCTCTTCC_1GCAGC$-3' (SEQ ID NO: 8), and 5'-$G_1TC_1GCCCCTTCTCCCC_1GCAG_1C$-3' (SEQ ID NO: 7), wherein $C_1$ is 5-methyl-dC and $G_1$ is 2'-deoxyguanosine methylphosphonate.

A method for inhibiting the activity of a TLR9 agonist comprising administering a compound comprising the sequence (SEQ ID NO: 1): 5'-$(N_1)_mCG(N_2)_p$-3', wherein $N_1$ and $N_2$ are independently any nucleotide, m is number from 0 to about 5, p is a number from about 6 to about 35, C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; and provided that at each instance that $N_1$ and/or $N_2$ comprise a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto. In some embodiments, the compounds and compositions that preferentially antagonize, inhibit, suppress or prevent the activity of TLR9 have the following sequence (SEQ ID NO: 2): 5'-$(N_1)_nCG(N_2)_rCG(N_3)_z$-3', wherein $N_1$, $N_2$, and $N_3$ are independently any nucleotide, n is 2, r is 11, z is 3, C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto, and provided that at each instance that $N_1$, $N_2$ and/or $N_3$ comprise a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto. In preferred embodiments, the compound is selected from the group consisting of 5'-$GTC_1GCCCCTTCTCCCC_1GCAG$-3', 5'-$GTC_1GCCCCTTCTCCCC_1GCAGC$-3', 5'-$G_1TC_1GCCCCTTCTCCCC_1GCAG_1$-3', 5'-$GTC_1GTTTACCTCTTCC_1GCAGC$-3', and 5'-$G_1TC_1GCCCCTTCTCCCC_1GCAG_1C$-3', wherein $C_1$ is 5-methyl-dC and $G_1$ is 2'-deoxyguanosine methylphosphonate.

In some embodiments, the invention provides a method for inhibiting the activity of a TLR9 agonist comprising administering a compound comprising the sequence 5'-$G_xTC*G*(N_1)_mCC*G*CAG_x(N_2)_p$-3' (SEQ ID NO: 3), wherein Gx is 2'-deoxyguanosine or 2'-deoxyguanosine methylphosphonate, $N_1$ is any nucleotide and $N_2$ is any nucleotide, wherein m is 10 and p is 0 or 1, and wherein C* is a nucleotide comprising a nitrogenous base selected from the group consisting of cytosine, 5-methyl-2'-deoxycytosine and 2'-O-methylcytosine and G* is a nucleotide comprising a nitrogenous base selected from the group consisting of guanine, 5-methyl-2'-deoxyguanosine and 2'-O-methylguanine, provided that at least one of the nucleotides C* or G* comprises a methylated nitrogenous base; and provided that at each instance that $N_1$ comprises a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto. In preferred embodiments, the compound is selected from the group consisting of 5'-GTC$_1$GCCCCTTCTCCCC$_1$GCAG-3' (SEQ ID NO: 4), 5'-GTC$_1$GCCCCTTCTCCCC$_1$GCAGC-3' (SEQ ID NO: 5), 5'-G$_1$TC$_1$GCCCCTTCTCCCC$_1$GCAG$_1$-3' (SEQ ID NO: 6), 5'-GTC$_1$GTTTACCTCTTCC$_1$GCAGC-3' (SEQ ID NO: 8), and 5'-G$_1$TC$_1$GCCCCTTCTCCCC$_1$GCAG$_1$C-3' (SEQ ID NO: 7), wherein C$_1$ is 5-methyl-dC and G$_1$ is 2'-deoxyguanosine methylphosphonate.

The invention further provides methods for therapeutically treating a patient, such methods comprising administering to the patient a compound according to the invention comprising the sequence (SEQ ID NO: 1): 5'-(N$_1$)$_m$CG(N$_2$)$_p$-3', wherein N$_1$ and N$_2$ are independently any nucleotide, m is number from 0 to about 5, p is a number from about 6 to about 35, C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; and provided that at each instance that N$_1$ and/or N$_2$ comprise a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto. In some embodiments, the compounds and compositions that preferentially antagonize, inhibit, suppress or prevent the activity of TLR9 have the following sequence (SEQ ID NO: 2): 5'-(N$_1$)$_n$CG(N$_2$)$_r$CG(N$_3$)$_z$-3', wherein N$_1$, N$_2$, and N$_3$ are independently any nucleotide, n is 2, r is 11, z is 3, C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto, and provided that at each instance that N$_1$, N$_2$ and/or N$_3$ comprise a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto. In preferred embodiments, the compound is selected from the group consisting of 5'-GTC$_1$GCCCCTTCTCCCC$_1$GCAG-3, 5'-GTC$_1$GCCCCTTCTCCCC$_1$GCAGC-3', 5'-G$_1$TC$_1$GCCCCTTCTCCCC$_1$GCAG$_1$-3', 5'-GTC$_1$GTTTACCTCTTCC$_1$GCAGC-3', and 5'-G$_1$TC$_1$GCCCCTTCTCCCC$_1$GCAG$_1$C-3', wherein C$_1$ is 5-methyl-dC and G$_1$ is 2'-deoxyguanosine methylphosphonate. In some embodiments the patient has a disease or disorder. In some embodiments, the disease or disorder is mediated by a toll-like receptor (TLR). In some embodiments, the disease or disorder is mediated by TLR9.

In some embodiments, the invention provides methods for therapeutically treating a patient, such methods comprising administering to the patient a compound according to the invention comprising the sequence 5'-G$_x$TC*G*(N$_1$)$_m$CC*G*CAG$_x$(N$_2$)$_p$-3' (SEQ ID NO: 3), wherein Gx is 2'-deoxyguanosine or 2'-deoxyguanosine methylphosphonate, N$_1$ is any nucleotide and N$_2$ is any nucleotide, wherein m is 10 and p is 0 or 1, and wherein C* is a nucleotide comprising a nitrogenous base selected from the group consisting of cytosine, 5-methyl-2'-deoxycytosine and 2'-O-methylcytosine and G* is a nucleotide comprising a nitrogenous base selected from the group consisting of guanine, 5-methyl-2'-deoxyguanosine and 2'-O-methylguanine, provided that at least one of the nucleotides C* or G* comprises a methylated nitrogenous base; and provided that at each instance that N$_1$ comprises a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto. In preferred embodiments, the compound is selected from the group consisting of 5'-GTC$_1$GCCCCTTCTCCCC$_1$GCAG-3' (SEQ ID NO: 4), 5'-GTC$_1$GCCCCTTCTCCCC$_1$GCAGC-3' (SEQ ID NO: 5), 5'-G$_1$TC$_1$GCCCCTTCTCCCC$_1$GCAG$_1$-3' (SEQ ID NO: 6), 5'-GTC$_1$GTTTACCTCTTCC$_1$GCAGC-3' (SEQ ID NO: 8), and 5'-G$_1$TC$_1$GCCCCTTCTCCCC$_1$GCAG$_1$C-3' (SEQ ID NO: 7), wherein C$_1$ is 5-methyl-dC and G$_1$ is 2'-deoxyguanosine methylphosphonate. In some embodiments, the patient has a disease or disorder. In some embodiments, the disease or disorder is mediated by a toll-like receptor (TLR). In some embodiments, the disease or disorder is mediated by TLR9.

In various embodiments, the disease or disorder to be treated is cancer, an autoimmune disorder, airway inflammation, inflammatory disorders, infectious disease, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma or a disease caused by a pathogen. Preferred autoimmune disorders include without limitation lupus erythematosus, multiple sclerosis, type I diabetes mellitus, irritable bowel syndrome, Crohn's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis ("giant cell arteritis"), vasculitis, vitiligo, vulvodynia and Wegener's granulomatosis. Preferred inflammatory disorders include without limitation airway inflammation, asthma, autoimmune diseases, chronic inflammation, chronic prostatitis, glomerulonephritis, Behçet's disease, hypersensitivities, inflammatory bowel disease, reperfusion injury, rheumatoid arthritis, transplant rejection, ulcerative colitis, uveitis, conjunctivitis and vasculitis. Pathogens include bacteria, parasites, fungi, viruses, viroids, and prions. In some embodiments, the disease or disorder is mediated by a TLR9-induced immune response. In some embodiments the disease is selected from ulcerative colitis, Crohn's disease, and inflammatory bowel disease. In some embodiments the disease is ulcerative colitis. In some embodiments the disease is Crohn's disease. In some embodiments the disease is inflammatory bowel disease.

The invention further provides methods for preventing disease or disorder, such methods comprising administering to the patient a compound according to the invention comprising the sequence (SEQ ID NO: 1): 5'-$(N_1)_m CG(N_2)_p$-3', wherein $N_1$ and $N_2$ are independently any nucleotide, m is number from 0 to about 5, p is a number from about 6 to about 35, C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; and provided that at each instance that $N_1$ and/or $N_2$ comprise a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto. In some embodiments, the compounds and compositions that preferentially antagonize, inhibit, suppress or prevent the activity of TLR9 have the following sequence (SEQ ID NO: 2): 5'-$(N_1)_n CG(N_2)_r CG(N_3)_z$-3', wherein $N_1$, $N_2$, and $N_3$ are independently any nucleotide, n is 2, r is 11, z is 3, C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto, and provided that at each instance that $N_1$, $N_2$ and/or $N_3$ comprise a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto. In preferred embodiments, the compound is selected from the group consisting of 5'-GTC$_1$GCCCCTTCTCCCC$_1$GCAG-3, 5'-GTC$_1$GCCCCTTCTCCCC$_1$GCAGC-3', 5'-G$_1$TC$_1$GCCCCTTCTCCCC$_1$GCAG$_1$-3', 5'-GTC$_1$GTTTACCTCTTCC$_1$GCAGC-3', and 5'-G$_1$TC$_1$GCCCCTTCTCCCC$_1$GCAG$_1$C-3', wherein $C_1$ is 5-methyl-dC and $G_1$ is 2'-deoxyguanosine methylphosphonate. In some embodiments, the disease or disorder is mediated by a toll-like receptor (TLR). In some embodiments, the disease or disorder is mediated by TLR9.

The invention further provides methods for preventing disease or disorder, such methods comprising administering to the patient a compound according to the invention comprising the sequence 5'-$G_x TC*G*(N_1)_m CC*G*CAG_x(N_2)_p$-3' (SEQ ID NO: 3), wherein Gx is 2'-deoxyguanosine or 2'-deoxyguanosine methylphosphonate, $N_1$ is any nucleotide and $N_2$ is any nucleotide, wherein m is 10 and p is 0 or 1, and wherein C* is a nucleotide comprising a nitrogenous base selected from the group consisting of cytosine, 5-methyl-2'-deoxycytosine and 2'-O-methylcytosine and G* is a nucleotide comprising a nitrogenous base selected from the group consisting of guanine, 5-methyl-2'-deoxyguanosine and 2'-O-methylguanine, provided that at least one of the nucleotides C* or G* comprises a methylated nitrogenous base; and provided that at each instance that $N_1$ comprises a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto. In preferred embodiments, the compound is selected from the group consisting of 5'-GTC$_1$GCCCCTTCTCCCC$_1$GCAG-3' (SEQ ID NO: 4), 5'-GTC$_1$GCCCCTTCTCCCC$_1$GCAGC-3' (SEQ ID NO: 5), 5'-G$_1$TC$_1$GCCCCTTCTCCCC$_1$GCAG$_1$-3' (SEQ ID NO: 6), 5'-GTC$_1$GTTTACCTCTTCC$_1$GCAGC-3' (SEQ ID NO: 8), and 5'-G$_1$TC$_1$GCCCCTTCTCCCC$_1$GCAG$_1$C-3' (SEQ ID NO: 7), wherein $C_1$ is 5-methyl-dC and $G_1$ is 2'-deoxyguanosine methylphosphonate. In some embodiments, the disease or disorder is mediated by a toll-like receptor (TLR). In some embodiments, the disease or disorder is mediated by TLR9.

In various embodiments, the disease or disorder to be prevented is cancer, an autoimmune disorder, airway inflammation, inflammatory disorders, infectious disease, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma or a disease caused by a pathogen. Preferred autoimmune disorders include without limitation lupus erythematosus, multiple sclerosis, type I diabetes mellitus, irritable bowel syndrome, Crohn's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis ("giant cell arteritis"), vasculitis, vitiligo, vulvodynia and Wegener's granulomatosis. Preferred inflammatory disorders include without limitation airway inflammation, asthma, autoimmune diseases, chronic inflammation, chronic prostatitis, glomerulonephritis, Behçet's disease, hypersensitivities, inflammatory bowel disease, reperfusion injury, rheumatoid arthritis, transplant rejection, ulcerative colitis, uveitis, conjunctivitis and vasculitis. Pathogens include bacteria, parasites, fungi, viruses, viroids, and prions. In some embodiments, the disease or disorder is mediated by a TLR9-induced immune response. In some embodiments the disease is selected from ulcerative colitis, Crohn's disease, and inflammatory bowel disease. In some embodiments the disease is ulcerative colitis. In some embodiments the disease is Crohn's disease. In some embodiments the disease is inflammatory bowel disease.

Certain compounds according to the invention are shown in Table 2. In this table, the compounds have all phosphorothioate (PS) linkages, except where indicated. Except where indicated, all nucleotides are deoxyribonucleotides.

TABLE 2

| Compound # | Sequence/SEQ ID NO |
|---|---|
| 1 | 5'-GTC$_l$GCCCCTTCTCCCC$_l$GCAG-3/ SEQ ID NO: 4 |
| 2 | 5'-GTC$_l$GCCCCTTCTCCCC$_l$GCAGC-3'/ SEQ ID NO: 5 |
| 3 | 5'-G$_l$TC$_l$GCCCCTTCTCCCC$_l$GCAG$_l$-3'/ SEQ ID NO: 6 |
| 4 | 5'-G$_l$TC$_l$GCCCCTTCTCCCC$_l$GCAG$_l$C-3'/ SEQ ID NO: 7 |
| 5 | 5'-GTC$_l$GTTTACCTCTTCC$_l$GCAGC-3'/ SEQ ID NO: 8 |

C$_l$ = 5-methyl 2'-deoxycytidine 5'-monophosphate;
G$_l$ = 2'-deoxyguanosine methylphosphonate Certain control compounds are shown in Table 3. In this table, the compounds have all phosphorothioate (PS) linkages, except where indicated. Except where indicated, all nucleotides are deoxyribonucleotides.

TABLE 3

| Compound # | Sequence/SEQ ID NO |
|---|---|
| 6 | 5'-GTCGCCCCTTCTCCCCGCAG-3/SEQ ID NO: 9 |
| 7 | 5'-GTCGCCCCTTCTCCCCGCAGC-3/SEQ ID NO: 10 |
| 8 | 5'-5'-C$_l$TATC$_l$T<u>GU</u>C$_l$G$_2$TTC$_l$TC$_l$T<u>GU</u>-3'/ SEQ ID NO: 11 (TLR antagonist) |

C$_l$ = 5-methyl 2'-deoxycytidine 5'-monophosphate;
G$_2$ = 7-deaza-dG;
<u>G</u> = 2'-O-Me-G;
<u>U</u> = 2'-O-Me-U.

In some embodiments of any of the methods according to the invention, two oligonucleotides are covalently linked via a direct nucleotide to nucleotide linkage at their 3' ends through the 3' positions of the sugars or through a modified sugar or modified nucleobase or via a non-nucleotide linker at their 3' ends through the 3' positions of the sugars or through a modified sugar or modified nucleobase. In preferred aspects of this embodiment, at least one of the oligonucleotide is a compound according to the invention. In preferred embodiment, both oligonucleotides are compounds according to the invention. In preferred embodiments, the two oligonucleotides are covalently linked directly via a nucleotide linkage. In more preferred embodiments, the two oligonucleotides are covalently linked via a non-nucleotide linker.

As a non-limiting example, the non-nucleotide linker covalently linking the two oligonucleotides may be attached to the 3'-hydroxyl of the sugar. In such embodiments, the linker comprises a functional group, which is attached to the 3'-hydroxyl by means of a phosphate-based linkage like, for example, phosphodiester, phosphorothioate, phosphorodithioate, methylphosphonate, or by a non-phosphate-based linkage. Possible sites of conjugation for the linker to the 3' end of the oligonucleotide are indicated in Formula I, below, wherein B represents a heterocyclic base and wherein the arrow pointing to P indicates any attachment to phosphorous.

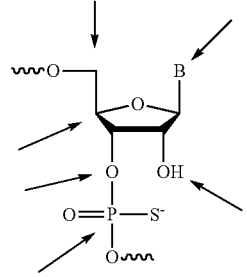

Formula I

In certain embodiments, the non-nucleotide linker is a small molecule, macromolecule or biomolecule, including, without limitation, polypeptides, antibodies, lipids, antigens, allergens, and oligosaccharides. In certain other embodiments, the non-nucleotide linker is a small molecule. For purposes of the invention, a small molecule is an organic moiety having a molecular weight of less than 1,000 Da. In some embodiments, the small molecule has a molecular weight of less than 750 Da.

In some embodiments, the small molecule is an aliphatic or aromatic hydrocarbon, either of which optionally can include, either in the linear chain connecting the oligonucleotides or appended to it, one or more functional groups including, but not limited to, hydroxy, amino, thiol, thioether, ether, amide, thioamide, ester, urea, or thiourea. The small molecule can be cyclic or acyclic. Examples of small molecule linkers include, but are not limited to, amino acids, carbohydrates, cyclodextrins, adamantane, cholesterol, haptens, and antibiotics. However, for purposes of describing the non-nucleotide linker, the term "small molecule" is not intended to include a nucleoside.

In some embodiments, the non-nucleotide linker is an alkyl linker or amino linker. The alkyl linker may be branched or unbranched, cyclic or acyclic, substituted or unsubstituted, saturated or unsaturated, chiral, achiral or racemic mixture. The alkyl linkers can have from about 2 to about 18 carbon atoms. In some embodiments such alkyl linkers have from about 2 to about 9 carbon atoms. In other embodiments, the alkyl linker has less than 3 carbon atoms. In further embodiments, the alkyl linker has at least 3 carbon atoms and preferentially more than three carbon atoms. Some alkyl linkers include one or more functional groups including, but not limited to, hydroxy, amino, thiol, thioether, ether, amide, thioamide, ester, urea, and thioether. Such alkyl linkers can include, but are not limited to, 1,2 propanediol, 1,2,3 propanetriol, 1,3 propanediol, 1,2,4-Butanetriol, 1,3,5-Pentanetriol, 3-trimethylamino-1,2-propanediol, Bis-1,5-O-(3' thymidyl(-1,3,5-pentanetriol, Bis-1,5-O-[3'-(1,2-dideoxy-D-robosyl)]-1,3,5-pentanetriol, 3-(2-Hydroxyethyl)-1,5-pentanediol, triethylene glycol hexaethylene glycol, polyethylene glycollinkers (e.g. [—O—CH2-CH2-]$_n$ (n=1-9)), methyl linkers, ethyl linkers, propyl linkers, butyl linkers or hexyl linkers. In some embodiments, such alkyl linkers may include peptides or amino acids.

In some embodiments, the non-nucleotide linker may include, but are not limited to, those listed in Table 3.

TABLE 3

Representative Non-Nucleotidic Linkers

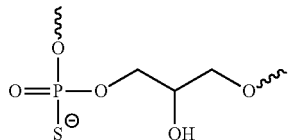

1,2,3-Propanediol linker (glycerol)

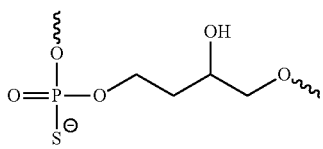

1,2,4-Butanetriol Linker

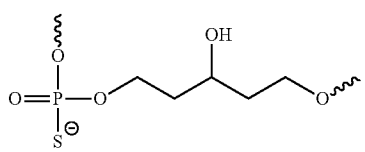

1,3,5-Pentanetriol Linker

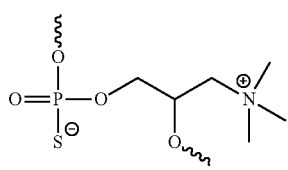

3-Trimethylamino-1,2-propanediol Linker

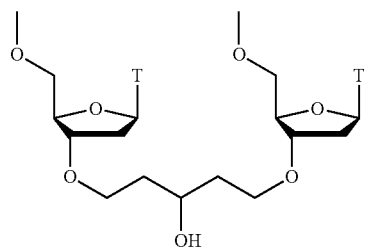

Bis-1,5-O-(3'-thymidyl)-1,3,5-pentanetriol Linker

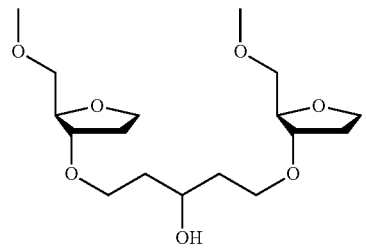

Bis-1,5-O-[3'-(1,2-dideoxy-D-ribosyl)]-1,3-5-pentanetriol Linker

TABLE 3-continued

Representative Non-Nucleotidic Linkers

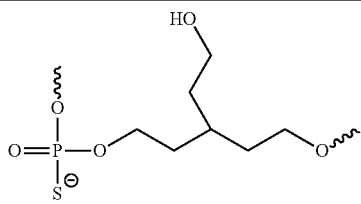

3-(2-Hydroxyethyl)-1,5-pentanediol Linker

In some embodiments, the small molecule linker is glycerol or a glycerol homolog of the formula HO—$(CH_2)_o$—CH(OH)—$(CH_2)_p$—OH, wherein o and p independently are integers from 1 to about 6, from 1 to about 4, or from 1 to about 3. In some other embodiments, the small molecule linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6, or from 2 to about 4.

Some non-nucleotide linkers permit attachment of more than two oligonucleotides. For example, the small molecule linker glycerol has three hydroxyl groups to which oligonucleotides may be covalently attached. Some compounds according to the invention, therefore, comprise two or more oligonucleotides linked to a nucleotide or a non-nucleotide linker. Such compounds are referred to as being "branched".

In any of the methods according to the invention, the compounds can be combined with one or more vaccines, antigens, antibodies, cytotoxic agents, allergens, antibiotics, antisense oligonucleotides, TLR agonist, TLR antagonist, peptides, proteins, gene therapy vectors, DNA vaccines, adjuvants or kinase inhibitors to enhance the specificity or magnitude of the immune response, or co-stimulatory molecules such as cytokines, chemokines, protein ligands, transactivating factors, peptides and peptides comprising modified amino acids.

In any of the methods according to the invention, administration of the compound according to the invention can be by any suitable route, including, without limitation, parenteral, mucosal delivery, oral, sublingual, transdermal, topical, inhalation, intragastric, intranasal, aerosol, intraocular, intratracheal, intrarectal, vaginal, by gene gun, dermal patch or in eye drop or mouthwash form. Administration of the therapeutic compositions of the compound can be carried out using known procedures at dosages and for periods of time effective to reduce symptoms or surrogate markers of the disease. When administered systemically, the therapeutic composition is preferably administered at a sufficient dosage to attain a blood concentration of compound from about 0.0001 micromolar to about 100 micromolar. More preferably, systemic administration would be at a sufficient dosage to attain a blood concentration of the compound from about 0.001 micromolar to about 10 micromolar. For localized administration, much lower concentrations than this may be effective, and much higher concentrations may be tolerated. Preferably, a total dosage of the compound ranges from about 0.001 mg per patient per day to about 200 mg per kg body weight per day. It may be desirable to administer the compound according to the invention daily, every second day, every third day, every fourth day, every fifth day, every sixth day or weekly. It may be desirable to administer simultaneously, or sequentially, a therapeutically effective amount of one or more of the containing therapeutic compositions of the invention to an individual as a single treatment episode.

The methods according to the invention are useful for model studies of the immune system. The methods are also useful for the prophylactic or therapeutic treatment of human or animal disease. For example, the methods are useful for pediatric, adult, and veterinary vaccine applications.

In any of the methods according to the invention, the compound can be administered in combination with any other agent useful for treating or preventing the disease or condition that does not abolish the immune antagonist, inhibitory, suppression or prevention effect or activity of the compound. In any of the methods according to the invention, the agent useful for treating or preventing the disease or condition includes, but is not limited to, one or more vaccines, antigens, antibodies, cytotoxic agents, allergens, antibiotics, antisense oligonucleotides, TLR agonist, TLR antagonist, peptides, proteins, gene therapy vectors, DNA vaccines, adjuvants or kinase inhibitors to enhance the specificity or magnitude of the immune response, or co-stimulatory molecules such as cytokines, chemokines, protein ligands, trans-activating factors, peptides and peptides comprising modified amino acids. For example, in the treatment of cancer, it is contemplated that the compound may be administered in combination with one or more chemotherapeutic compound, targeted therapeutic agent and/or monoclonal antibody; and in preventing a disease, it is contemplated that the compound may be administered in combination with one or more vaccine.

In some embodiments, the invention provides a pharmaceutical composition comprising a compound according to the invention and a physiologically acceptable carrier. In some embodiments, the composition can further comprise one or more vaccines, antigens, antibodies, cytotoxic agents, allergens, antibiotics, antisense oligonucleotides, TLR agonist, TLR antagonist, peptides, proteins, gene therapy vectors, DNA vaccines, adjuvants or kinase inhibitors to enhance the specificity or magnitude of the immune response, or co-stimulatory molecules such as cytokines, chemokines, protein ligands, trans-activating factors, peptides and peptides comprising modified amino acids.

The following examples are intended to further illustrate certain exemplary embodiments of the invention and are not intended to limit the scope of the invention. For example, representative TLR-ligands are shown in the following examples, but do not limit the scope of ligands to which the compounds of the invention act as antagonists.

EXAMPLE 1

Compounds of the Invention Do Not Induce a TLR9-Mediated Immune Response

C57 BL/6 mice (female, n=3) were injected subcutaneously with 40 mg/kg of compound 8 (control TLR antagonist), compound 2, compound 7, compound 5 (10 nt mismatch with compound 2) or PBS. Serum samples were collected 2 hours after injection. Serum IL-12 level was determined by a mouse specific IL-12 ELISA. Results are shown in FIG. 1.

EXAMPLE 2

Compounds of the Invention are Antagonist of TLR9

Figure 2:
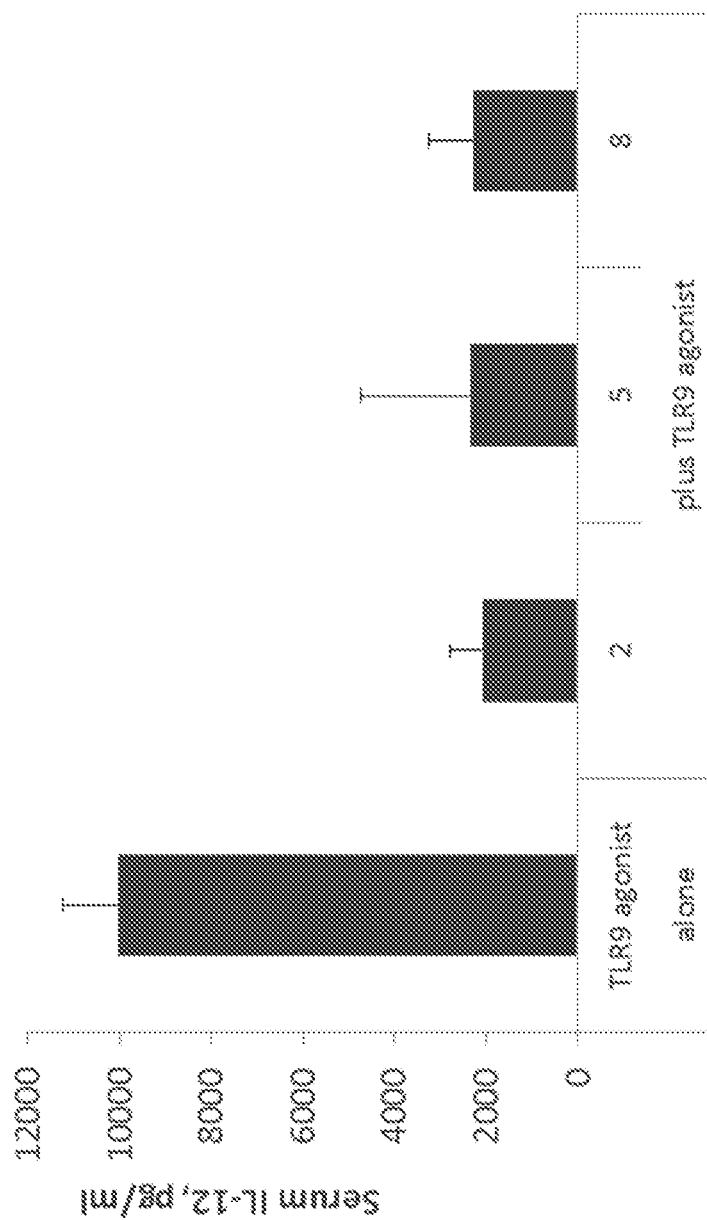
FIG. 2 depicts the ability of TLR9 antagonists according to the invention to inhibit TLR9-induced IL-12 in vivo in mice.

C57 BL/6 mice (female, n=3) were injected subcutaneously with 10 mg/kg of compound 8 (control TLR antagonist), compound 2, compound 5 (10 nt mismatch with compound 2) or PBS. All mice were injected subcutaneously with 0.25 mg/kg of TLR9 agonist. Serum samples were collected 2 hours after TLR9 agonist administration. Serum IL-12 level was determined by a mouse specific IL-12 ELISA. Results are shown in FIG. 2.

Figure 3:
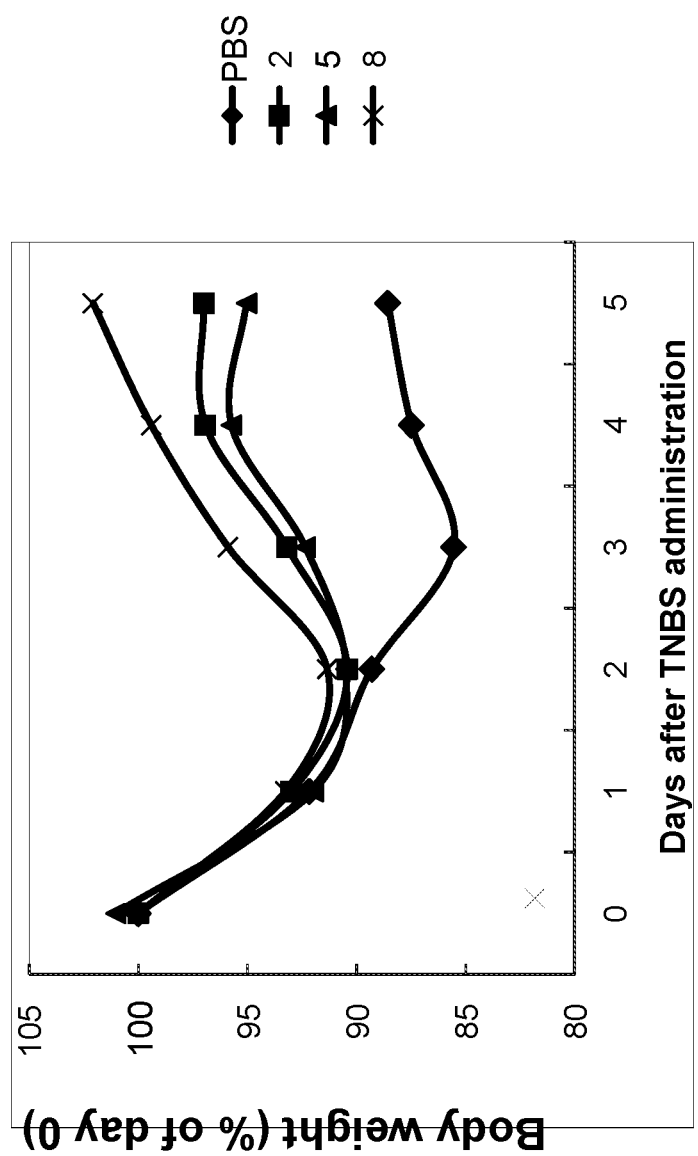
FIG. 3 depicts the % body weight change in a TNBS-induced colitis mouse model after administration of compounds according to the invention.

SJL/J mice (female, n=10) were intrarectally administered with 2.5 mg 2,4,6-trinitrobenzene sulfonic acid (TNBS, Sigma-Aldrich, St. Louis, Mo.) in 100 μl of 50% ethanol on day 0. On day 1, mice were intragastrically administered with 200 ml (15 mg/kg) of compound 8 (TLR antagonist), compound 2, compound 5 (10 nt mismatch with compound 2) or PBS. All mice were monitored for body weight change daily. Results are shown in FIG. 3.

Figure 4:
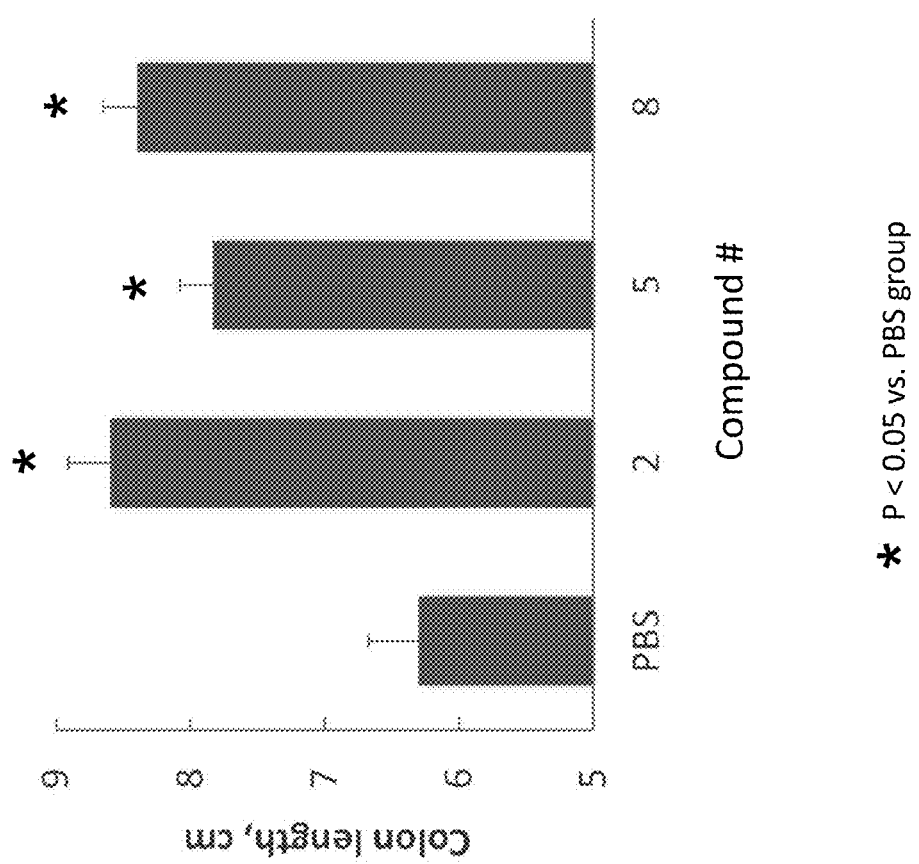
FIG. 4 depicts the colon length in a TNBS-induced colitis mouse model after administration of compounds according to the invention.
Figure 5:
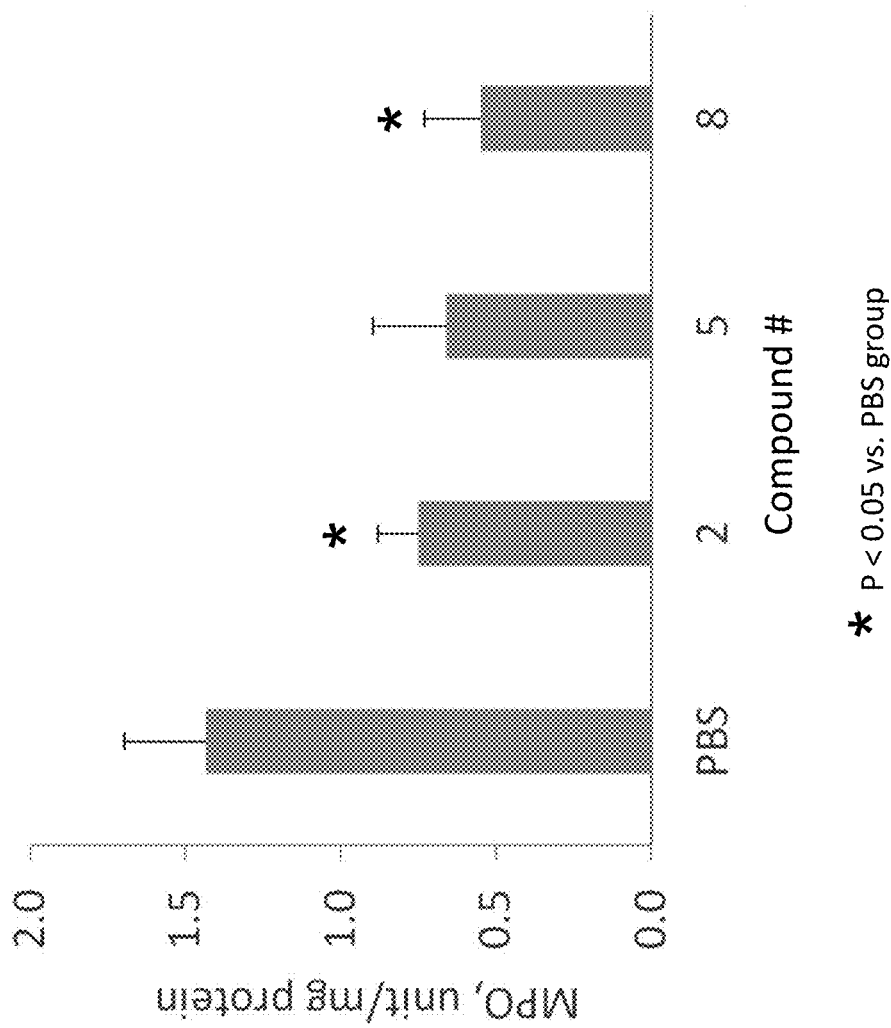
FIG. 5 depicts colon myeloperoxidase levels in a TNBS-induced colitis mouse model after administration of compounds according to the invention.

On day 7, all mice were sacrificed, colon length were measured by a caliper and colon samples were collected. Some of the colon samples were homogenated and colon myeloperoxidase (MPO) levels were evaluated using a MPO colorimetric assay kit (Sigma-Aldrich). Asterisk indicates $p<0.05$ when compared to PBS group. Statistical analysis was done by unpaired two-tailed Student's t test. Results are shown in FIGS. 4 and 5.

Figure 6:
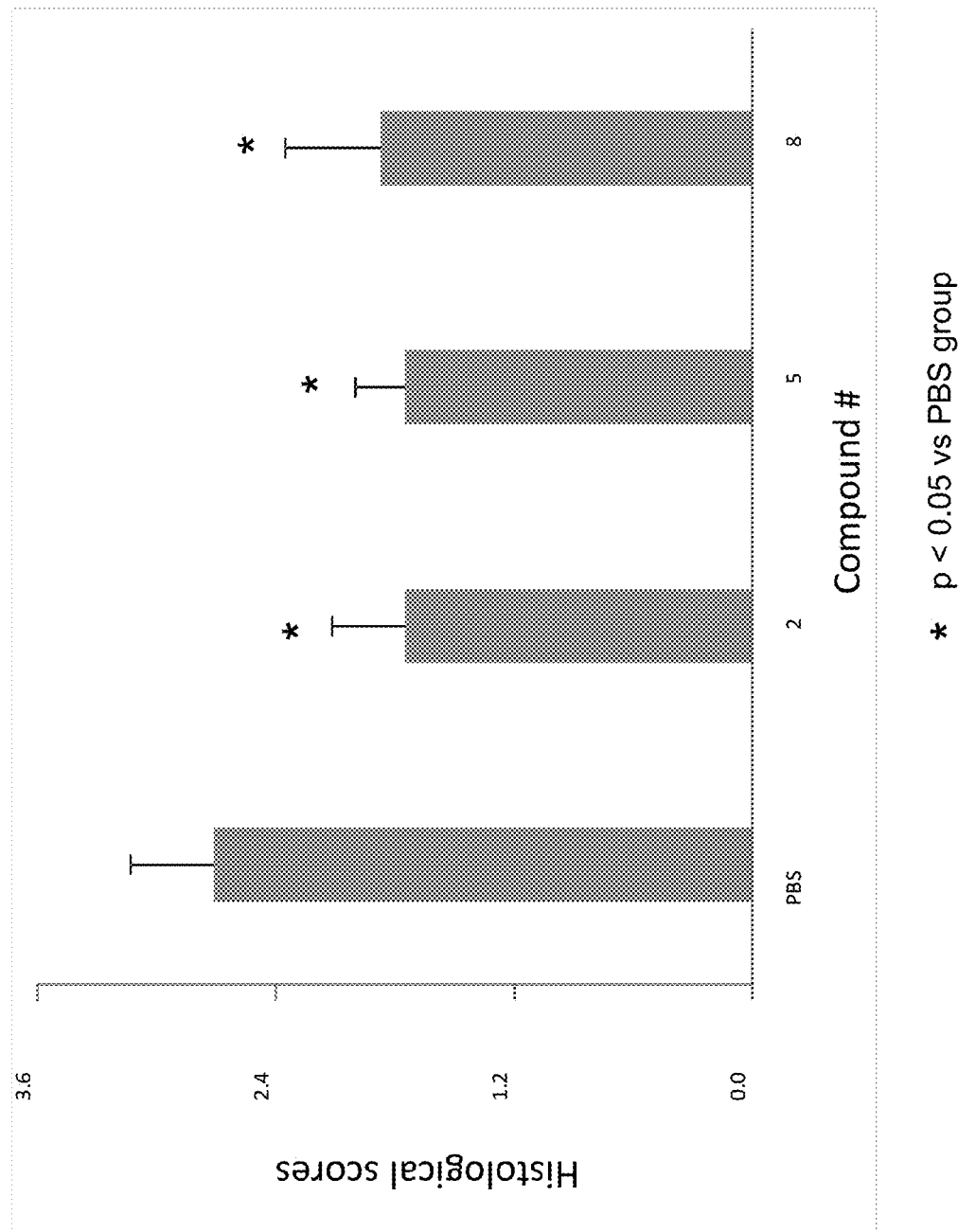
FIG. 6 depicts the colon histological score in a TNBS-induced colitis mouse model after administration of compounds according to the invention.

Additionally, some of the colon samples were fixed with 10% formalin and sectioned. Colon histology was evaluated (0: no evidence of inflammation; 1: leucocyte infiltration in a <10% high-power field (hpf), no structural changes observed; 2: leucocyte infiltration in 10-25% hpf, crypt elongation, intestinal wall thickening which does not extend beyond mucosal layer; 3: leucocyte infiltration in 25-50% hpf, thickening of intestinal wall which extends beyond mucosal layer; 4: leucocyte infiltration in >50% hpf, mucosal structure distortion, transmural intestinal wall thickening with ulceration.) Asterisk indicates $p<0.05$ when compared to PBS group. Statistical analysis was done by unpaired two-tailed Student's t test. Results are shown in FIG. 6.

Some of the colon samples were stored in RNAlater (Life Technologies, Grand Island, N.Y.). Total RNA was isolated using MagMax (Life Technologies) according to manufacturer's suggestion. 1 mg RNA was reverse transcribed to cDNA using High-Capacity RNA-to-cDNA kit (Life Technologies). Gene expression was determined using a mouse Crohn's disease PCR array (QIAGEN, Valencia, Calif.). Gene expression levels were normalized to naïve SJL/J mice (n=3). Mean of Log2 fold change were shown in FIG. 7.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for inhibiting a TLR9-mediated immune response in a mammal, the method comprising administering an effective amount of a compound to inhibit the TLR-mediated immune response, wherein the compound comprises the sequence 5'-$G_x$TC*G*($N_1$)$_m$CC*G*CAG$_x$($N_2$)$_p$-3' (SEQ ID NO: 3), wherein Gx is 2'-deoxyguanosine or 2'-deoxyguanosine methylphosphonate, $N_1$ is any nucleotide and $N_2$ is any nucleotide, wherein m is 10 and p is 0 or 1, and wherein C* is a nucleotide comprising a nitrogenous base selected from the group consisting of cytosine, 5-methyl-2'-deoxycytosine and 2'-O-methylcytosine and G* is a nucleotide comprising a nitrogenous base selected from the group consisting of guanine, 5-methyl-2'deoxyguanosine and 2'-O-methylguanine, provided that at least one of the nucleotides C* or G* comprises a methylated nitrogenous base; and provided that at each instance that $N_1$ comprises a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto.

2. The method according to claim 1, wherein the compound is selected from the group consisting of 5'-GTC$_1$GCCCCTTCTCCCC$_1$GCAG-3' (SEQ ID NO: 4), 5'-GTC$_1$GCCCCTTCTCCCC$_1$GCAGC-3' (SEQ ID NO: 5), 5'-G$_1$TC$_1$GCCCCTTCTCCCC$_1$GCAG$_1$-3' (SEQ ID NO: 6), 5'-GTC$_1$GTTTACCTCTTCC$_1$GCAGC-3' (SEQ ID NO: 8), and 5'-G$_1$TC$_1$G CCCCTTCTCCCC$_1$GCAG$_1$C-3' (SEQ ID NO: 7), wherein C$_1$ is 5-methyl-dC and G$_1$ is 2'-deoxyguanosine methylphosphonate.

3. The method according to claim 1, wherein the route of administration is parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form.

4. The method according to claim 1, wherein the mammal is a human.

5. The method according to claim 1, wherein the compound is administered in combination with one or more vaccines, antigens, antibodies, cytotoxic agents, allergens, antibiotics, antisense oligonucleotides, TLR agonists, TLR antagonists, peptides, proteins, gene therapy vectors, DNA vaccines, adjuvants, kinase inhibitors or co-stimulatory molecules.

6. A method for inhibiting the activity of a TLR9 agonist comprising administering an effective amount of a compound to inhibit the activity of a TLR9 agonist, wherein the compound comprises the sequence 5'-$G_x$TC*G*($N_1$)$_m$CC*G*CAG$_x$($N_2$)$_p$-3' (SEQ ID NO: 3), wherein Gx is 2'-deoxyguanosine or 2'-deoxyguanosine methylphosphonate, $N_1$ is any nucleotide and $N_2$ is any nucleotide, wherein m is 10 and p is 0 or 1, and wherein C* is a nucleotide comprising a nitrogenous base selected from the group consisting of cytosine, 5-methyl-2'-deoxycytosine and 2'-O-methylcytosine and G* is a nucleotide comprising a nitrogenous base selected from the group consisting of guanine, 5-methyl-2'-deoxyguanosine and 2'-O-methylguanine, provided that at least one of the nucleotides C* or G* comprises a methylated nitrogenous base; and provided that at each instance that $N_1$ comprises a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto.

7. The method according to claim 6, wherein the compound is selected from the group consisting of 5'-GTC$_1$GCCCCTTCTCCCC$_1$GCAG-3' (SEQ ID NO: 4), 5'-GTC$_1$GCCCCTTCTCCCC$_1$GCAGC-3' (SEQ ID NO: 5), 5'-G$_1$TC$_1$GCCCCTTCTCCCC$_1$GCAG$_1$-3' (SEQ ID NO: 6), 5'-GTC$_1$GTTTACCTCTTCC$_1$GCAGC-3' (SEQ ID NO: 8), and 5'-G$_1$TC$_1$GCCCCTTCTCCCC$_1$GCAG$_1$C-3' (SEQ ID NO: 7), wherein C$_1$ is 5-methyl-dC and G$_1$ is 2'-deoxyguanosine methylphosphonate.

8. The method according to claim 6, wherein the route of administration is parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form.

9. The method according to claim 6, wherein the compound is administered in combination with one or more vaccines, antigens, antibodies, cytotoxic agents, allergens, antibiotics, antisense oligonucleotides, TLR antagonists, peptides, proteins, gene therapy vectors, DNA vaccines, adjuvants, kinase inhibitors or co-stimulatory molecules.

10. A method for therapeutically treating a mammal, such method comprising administering an effective amount of a compound comprising the sequence 5'-$G_x$TC*G*($N_1$)$_m$CC*G*CAG$_x$($N_2$)$_p$-3' (SEQ ID NO: 3), wherein Gx is 2'-deoxyguanosine or 2'-deoxyguanosine methylphosphonate, $N_1$ is any nucleotide and $N_2$ is any nucleotide, wherein m is 10 and p is 0 or 1, and wherein C* is a nucleotide comprising a nitrogenous base selected from the group consisting of cytosine, 5-methyl-2'-deoxycytosine and 2'-O-methylcytosine and G* is a nucleotide comprising a nitrogenous base selected from the group consisting of guanine, 5-methyl-2'-deoxyguanosine and 2'-O-methylguanine, provided that at least one of the nucleotides C* or G* comprises a methylated nitrogenous base; and provided that at each instance that $N_1$ comprises a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto; and wherein the compound inhibits a TLR9-mediated immune response.

11. The method according to claim 10, wherein the compound is selected from the group consisting of 5'-GTC$_1$GCCCCTTCTCCCC$_1$GCAG-3' (SEQ ID NO: 4), 5'-GTC$_1$GCCCCTTCTCCCC$_1$GCAGC-3' (SEQ ID NO: 5), 5'-G$_1$TC$_1$GCCCCTTCTCCCC$_1$GCAG$_1$-3' (SEQ ID NO: 6), 5'-GTC$_1$GTTTACCTCTTCC$_1$GCAGC-3' (SEQ ID NO: 8), and 5'-G$_1$TC$_1$GCCCCTTCTCCCC$_1$GCAG$_1$C-3' (SEQ ID NO: 7), wherein C$_1$ is 5-methyl-dC and G$_1$ is 2'-deoxyguanosine methylphosphonate.

12. The method according to claim 10, wherein the mammal has an autoimmune disease.

13. The method according to claim 12, wherein the autoimmune disease is selected from psoriasis, rheumatoid arthritis, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjogren's syndrome, temporal arteritis, vasculitis, vitiligo, vulvodynia or Wegener's granulomatosis.

14. The method according to claim 10, wherein the compound is administered in combination with one or more vaccines, antigens, antibodies, cytotoxic agents, allergens, antibiotics, antisense oligonucleotides, TLR agonists, TLR antagonists, peptides, proteins, gene therapy vectors, DNA vaccines, adjuvants, kinase inhibitors or co-stimulatory molecules.

15. The method according to claim 10, wherein the route of administration is parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form.

16. The method according to claim 10, wherein the mammal is a human.

17. A method for preventing disease, such method comprising administering to a mammal a compound comprising the sequence 5'-G$_x$TC*G*(N$_1$)$_m$CC*G*CAGx(N$_2$)$_p$-3' (SEQ ID NO: 3), wherein Gx is 2'-deoxyguanosine or 2'-deoxyguanosine methylphosphonate, N$_1$ is any nucleotide and N$_2$ is any nucleotide, wherein m is 10 and p is 0 or 1, and wherein C* is a nucleotide comprising a nitrogenous base selected from the group consisting of cytosine, 5-methyl-2'-deoxycytosine and 2'-O-methylcytosine and G* is a nucleotide comprising a nitrogenous base selected from the group consisting of guanine, 5-methyl-2'-deoxyguanosine and 2'-O-methylguanine, provided that at least one of the nucleotides C* or G* comprises a methylated nitrogenous base; and provided that at each instance that N$_1$ comprises a CG dinucleotide C is a nucleotide comprising a nitrogenous base selected from the group consisting of cytosine, 5-methyl-2'-deoxycytosine and 2'-O-methylcytosine and G is a nucleotide comprising a nitrogenous base selected from the group consisting of guanine, 5-methyl-2'-deoxyguanosine and 2'-O-methylguanine, provided that at least one of the nucleotides C or G comprises a methylated nitrogenous base; or the complementary sequence thereto, and wherein the compound inhibits a TLR9-mediated immune response.

18. The method according to claim 17, wherein the compound is selected from the group consisting of 5'-GTC$_1$GCCCCTTCTCCCC$_1$GCAG-3' (SEQ ID NO: 4), 5'-GTC$_1$GCCCCTTCTCCCC$_1$GCAGC-3' (SEQ ID NO: 5), 5'-G$_1$TC$_1$GCCCCTTCTCCCC$_1$GCAG$_1$-3' (SEQ ID NO: 6), 5'-GTC$_1$GTTTACCTCTTCC$_1$GCAGC-3' (SEQ ID NO: 8), and 5'-G$_1$TC$_1$GCCCCTTCTCCCC$_1$GCAG$_1$C-3' (SEQ ID NO: 7), wherein C$_1$ is 5-methyl-dC and G$_1$ is 2'-deoxyguanosine methylphosphonate.

19. The method according to claim 17, wherein the mammal has an autoimmune disease.

20. The method according to claim 19, wherein the autoimmune disease is selected from psoriasis, rheumatoid arthritis, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjogren's syndrome, temporal arteritis, vasculitis, vitiligo, vulvodynia or Wegener's granulomatosis.

21. The method according to claim 17, wherein the antagonist is administered in combination with one or more vaccines, antigens, antibodies, cytotoxic agents, allergens, antibiotics, antisense oligonucleotides, TLR agonists, TLR antagonists, peptides, proteins, gene therapy vectors, DNA vaccines, adjuvants or co-stimulatory molecules.

22. The method according to claim 17, wherein the route of administration is parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form.

23. The method according to claim 17, wherein the mammal is a human.

* * * * *

SEQUENCE LISTING

<160> NUMBER OF SEQ ID NOS: 11

<210> SEQ ID NO 1

```
<211> LENGTH: 4
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: N = A,T,C or G
<220> FEATURE:
<221> NAME/KEY: misc_feature
<222> LOCATION: (2)..(2)
<223> OTHER INFORMATION: C is a nitrogenous base selected from the group
      consisting of cytosine, 5-methyl-2'-deoxycytosine and
      2'-O-methylcytosine
<220> FEATURE:
<221> NAME/KEY: misc_feature
<222> LOCATION: (3)..(3)
<223> OTHER INFORMATION: G is a nitrogenous base selected from the group
      consisting of guanine, 5-methyl-2'-deoxyguanosine and
      2'-O-methylguanine
<220> FEATURE:
<221> NAME/KEY: misc_feature
<222> LOCATION: (4)..(4)
<223> OTHER INFORMATION: N = A,T,C or G

<400> SEQUENCE: 1 ncgn                                                                       4

<210> SEQ ID NO 2
<211> LENGTH: 7
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: N = A, T, C or G
<220> FEATURE:
<221> NAME/KEY: misc_feature
<222> LOCATION: (2)..(2)
<223> OTHER INFORMATION: C is a nitrogenous base selected from the group
      consisting of cytosine, 5-methyl-2'-deoxycytosine and
      2'-O-methylcytosine
<220> FEATURE:
<221> NAME/KEY: misc_feature
<222> LOCATION: (3)..(3)
<223> OTHER INFORMATION: G is a nitrogenous base selected from the group
      consisting of guanine, 5-methyl-2'-deo
<220> FEATURE:
<221> NAME/KEY: misc_feature
<222> LOCATION: (4)..(4)
<223> OTHER INFORMATION: N = A, T, C or G
<220> FEATURE:
<221> NAME/KEY: misc_feature
<222> LOCATION: (5)..(5)
<223> OTHER INFORMATION: C is a nitrogenous base selected from the group
      consisting of cytosine, 5-methyl-2'-deoxycytosine and
      2'-O-methylcytosine
<220> FEATURE:
<221> NAME/KEY: misc_feature
<222> LOCATION: (6)..(6)
<223> OTHER INFORMATION: G is a nitrogenous base selected from the group
      consisting of guanine, 5-methyl-2'-deo
<220> FEATURE:
<221> NAME/KEY: misc_feature
<222> LOCATION: (7)..(7)
<223> OTHER INFORMATION: N = A, T, C or G

<400> SEQUENCE: 2 ncgncgn                                                                    7

<210> SEQ ID NO 3
<211> LENGTH: 12
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 2'-deoxyguanosine or 2'-deoxyguanosine
      methylphosphonate
<220> FEATURE:
<221> NAME/KEY: misc_feature
<222> LOCATION: (3)..(3)
<223> OTHER INFORMATION: C is a nitrogenous base selected from the group
      consisting of cytosine, 5-methyl-2'-deoxycytosine and
      2'-O-methylcytosine
<220> FEATURE:
<221> NAME/KEY: misc_feature
<222> LOCATION: (4)..(4)
<223> OTHER INFORMATION: G is a nitrogenous base selected from the group
      consisting of guanine, 5-methyl-2'-deoxyguanosine and
      2'-O-methylguanine
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: C is a nitrogenous base selected from the group
      consisting of cytosine, 5-methyl-2'-deoxycytosine and
      2'-O-methylcytosine
<220> FEATURE:
<221> NAME/KEY: misc_feature
<222> LOCATION: (8)..(8)
<223> OTHER INFORMATION: G is a nitrogenous base selected from the group
      consisting of guanine, 5-methyl-2'-deoxyguanosine and
      2'-O-methylguanine
<220> FEATURE:
<221> NAME/KEY: misc_feature
<222> LOCATION: (11)..(11)
<223> OTHER INFORMATION: 2'-deoxyguanosine or 2'-deoxyguanosine
      methylphosphonate
<220> FEATURE:
<221> NAME/KEY: misc_feature
<222> LOCATION: (12)..(12)
<223> OTHER INFORMATION: 2'-deoxycytosine

<400> SEQUENCE: 3
gtcgnccgca gn                                                         12

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: C = 5-methyl 2'-deoxycytidine 5'-monophosphate
<220> FEATURE:
<221> NAME/KEY: misc_feature
<222> LOCATION: (16)..(16)
<223> OTHER INFORMATION: C = 5-methyl 2'-deoxycytidine 5'-monophosphate

<400> SEQUENCE: 4
gtcgcccctt ctccccgcag                                                 20

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (3)..(3)
<223> OTHER INFORMATION: C = 5-methyl 2'-deoxycytidine 5'-monophosphate
<220> FEATURE:
<221> NAME/KEY: misc_feature
<222> LOCATION: (16)..(16)
<223> OTHER INFORMATION: C = 5-methyl 2'-deoxycytidine 5'-monophosphate

<400> SEQUENCE: 5
gtcgcccctt ctccccgcag c                                              21

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 2'-deoxyguanosine methylphosphonate
<220> FEATURE:
<221> NAME/KEY: misc_feature
<222> LOCATION: (3)..(3)
<223> OTHER INFORMATION: C = 5-methyl 2'-deoxycytidine 5'-monophosphate
<220> FEATURE:
<221> NAME/KEY: misc_feature
<222> LOCATION: (16)..(16)
<223> OTHER INFORMATION: C = 5-methyl 2'-deoxycytidine 5'-monophosphate
<220> FEATURE:
<221> NAME/KEY: misc_feature
<222> LOCATION: (20)..(20)
<223> OTHER INFORMATION: 2'-deoxyguanosine methylphosphonate

<400> SEQUENCE: 6
gtcgcccctt ctccccgcag                                                20

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: G = 2'-deoxyguanosine methylphosphonate
<220> FEATURE:
<221> NAME/KEY: misc_feature
<222> LOCATION: (3)..(3)
<223> OTHER INFORMATION: C = 5-methyl 2'-deoxycytidine 5'-monophosphate
<220> FEATURE:
<221> NAME/KEY: misc_feature
<222> LOCATION: (16)..(16)
<223> OTHER INFORMATION: C = 5-methyl 2'-deoxycytidine 5'-monophosphate
<220> FEATURE:
<221> NAME/KEY: misc_feature
<222> LOCATION: (20)..(20)
<223> OTHER INFORMATION: G = 2'-deoxyguanosine methylphosphonate

<400> SEQUENCE: 7
gtcgcccctt ctccccgcag c                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: C = 5-methyl 2'-deoxycytidine 5'-monophosphate
```

```
<220> FEATURE:
<221> NAME/KEY: misc_feature
<222> LOCATION: (16)..(16)
<223> OTHER INFORMATION: C = 5-methyl 2'-deoxycytidine 5'-monophosphate

<400> SEQUENCE: 8
gtcgtttacc tcttccgcag c                                              21

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
gtcgcccctt ctccccgcag                                                20

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10
gtcgcccctt ctccccgcag c                                              21

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: C = 5-methyl 2'-deoxycytidine 5'-monophosphate
<220> FEATURE:
<221> NAME/KEY: misc_feature
<222> LOCATION: (5)..(5)
<223> OTHER INFORMATION: C = 5-methyl 2'-deoxycytidine 5'-monophosphate
<220> FEATURE:
<221> NAME/KEY: misc_feature
<222> LOCATION: (7)..(7)
<223> OTHER INFORMATION: G = 2'-O-Me-G
<220> FEATURE:
<221> NAME/KEY: misc_feature
<222> LOCATION: (8)..(8)
<223> OTHER INFORMATION: U = 2'-O-Me-U
<220> FEATURE:
<221> NAME/KEY: misc_feature
<222> LOCATION: (9)..(9)
<223> OTHER INFORMATION: C = 5-methyl 2'-deoxycytidine 5'-monophosphate
<220> FEATURE:
<221> NAME/KEY: misc_feature
<222> LOCATION: (10)..(10)
<223> OTHER INFORMATION: G =7-deaza-dG
<220> FEATURE:
<221> NAME/KEY: misc_feature
<222> LOCATION: (13)..(13)
<223> OTHER INFORMATION: C = 5-methyl 2'-deoxycytidine 5'-monophosphate
<220> FEATURE:
<221> NAME/KEY: misc_feature
<222> LOCATION: (15)..(15)
<223> OTHER INFORMATION: C = 5-methyl 2'-deoxycytidine 5'-monophosphate
<220> FEATURE:
<221> NAME/KEY: misc_feature
<222> LOCATION: (17)..(17)
<223> OTHER INFORMATION: G = 2'-O-Me-G
<220> FEATURE:
<221> NAME/KEY: misc_feature
<222> LOCATION: (18)..(18)
```

<223> OTHER INFORMATION: U = 2'-O-Me-U

<400> SEQUENCE: 11
ctatctgucg ttctctgu                                                18